United States Patent [19]
Zeiss

[11] Patent Number: 5,245,862
[45] Date of Patent: Sep. 21, 1993

[54] BALL TESTING DEVICE

[76] Inventor: Taylor R. Zeiss, 282 Kirksway Ct., Lake Orion, Mich. 48362

[21] Appl. No.: 813,253

[22] Filed: Dec. 24, 1991

[51] Int. Cl.[5] .............................. G01N 3/52
[52] U.S. Cl. ........................ 73/79; 73/12.01; 73/12.02
[58] Field of Search ..................... 73/12, 13, 79

[56] References Cited

U.S. PATENT DOCUMENTS

| | | |
|---|---|---|
| 3,093,995 | 6/1963 | Gordon . |
| 3,299,692 | 1/1967 | Mizejewski . |
| 3,496,765 | 2/1970 | Rathmell . |
| 3,509,736 | 5/1970 | Saari . |
| 3,576,127 | 4/1971 | Weitzel et al. . |
| 3,777,548 | 12/1973 | Nicolaides . |
| 4,006,626 | 2/1977 | Ruzicka et al. ............. 73/79 |
| 4,097,800 | 6/1978 | Kuchmas, Jr. et al. . |
| 4,411,153 | 10/1983 | Lewis ...................... 73/79 |
| 4,555,028 | 11/1985 | Valehrach . |
| 4,856,318 | 8/1989 | Hogan et al. ............... 73/12 |
| 4,876,658 | 10/1989 | Hass . |

Primary Examiner—Donald O. Woodiel
Assistant Examiner—R. Biegel
Attorney, Agent, or Firm—Gifford, Groh, Sprinkle, Patmore and Anderson

[57] ABSTRACT

A testing device and method for determining the coefficient of restitution of a rebounding object, such as a ball, by comparison of the bounce periods of successive bounces of the ball. The ball is dropped onto the reaction plate from which it is permitted to rebound at least three times. A transducer such as a microphone is mounted near the reaction plate to detect the impacts on the reaction plate. An electronic circuit times the interval or bounce period between impacts, stores the bounce periods for comparison. The coefficient of restitution for the rebounded object is determined by comparing a subsequent bounce interval to a preceding bounce period as a ratio. The coefficient of restitution so determined is displayed on an LCD display.

13 Claims, 3 Drawing Sheets

BALL TESTING DEVICE

BACKGROUND OF THE INVENTION

I. Field of the Invention

The present invention is directed to material testing, and more particularly, to a method and device for determining the coefficient of restitution of a rebounding object, such as a ball.

II. Description of the Prior Art

In many sports or games, the ability of a ball to travel or to be directed with precision is very important. It is well known that use reduces the effectiveness and quality of many balls. In many sports, such as golf, tennis, racquetball, or basketball, it is advantageous to determine the condition of the ball in advance in order to determine whether it is acceptable for use.

Rathmell U.S. Pat. No. 3,496,765 discloses a device which drops a ball on a curved surface to deflect the ball upwardly out through an aperture to land on a second curved surface. The ball is then deflected into a sand box for measurement. Rathmell also discloses a prior art testing device in which a ball is dropped from a standard height to a rebound surface A "good" ball follows a predetermined course to rebound through an opening to a second rebound surface and then to rebound through another opening. The trajectory of a "bad" ball prevents it from following the same course.

Nicolaides U.S. Pat. No. 3,777,548; Saari No. 3,509,736; and Mizeljewski No. 3,299,692 disclose impacting a ball with an anvil or the like and measuring the momentum of the ball when it contacts a target.

A third type of tester is disclosed in Gordon U.S. Pat. No. 3,093,995 in which the coefficient of restitution is measured by shooting a golf ball against a moveable target. The moveable target has a mass equal to that of a golf club.

However, the prior devices for quantifying the compression or rebound characteristics of golf balls have been large, complex structures. Such devices are large and expensive. Thus, it would be desirable to provide a device which is suitable for use by individuals or stores to test new or used balls prior to use.

SUMMARY OF THE PRESENT INVENTION

The present invention provides relatively inexpensive yet accurate method and apparatus for determining the coefficient of restitution of a rebounding object such as a ball. The method of the present invention for determining the coefficient of restitution includes the steps of dropping a ball on a reaction plate, permitting the ball to bounce on the reaction plate at least three times, detecting each impact of the object as it bounces on the reaction plate, measuring the time of the bounce interval between successive impacts, and computing the coefficient of restitution for the ball by comparing successive bounce intervals as a ratio of the time between impacts of the second bounce interval to that of the first interval.

The testing device for carrying out the method of the present invention includes a reaction plate which has a mass which is very large in comparison to the mass of the ball to be tested A transducer for registering each impact of the ball is mounted adjacent to the reaction plate. The transducer may be a microphone responsive to noise created by the impact or an accelerometer or strain gauge mounted on the reaction plate which produces a signal each time the ball impacts on the reaction plate.

Also provided is a display box having a display and electrical circuitry connected to the transducer. The circuitry includes a timer and a clock responsive to signals from the transducer to measure bounce intervals between successive impacts of the ball. The measurements of the successive bounce intervals are stored separately as voltages in capacitors. The voltages from the capacitors are connected to an A/D converter display driver which displays a ratio of the second bounce interval to the first interval on a LCD display. The ratio thus displayed is the coefficient of restitution for the ball.

In this way, a small, compact, and inexpensive device for measuring the coefficient of restitution of a ball is provided. Such a device may be provided for use in measuring the coefficient of restitution of any bouncing object. It is particularly suited for testing golf balls, tennis balls, racket balls and the like by individuals or in sporting goods stores. The testing device may be connected to a coin operated switch for use in stores.

BRIEF DESCRIPTION OF THE DRAWINGS

A better understanding of the present invention will now be had upon reference to the following detailed description, when read in conjunction with the accompanying drawing, wherein like reference characters refer to like parts through the several views and in which.

DETAILED DESCRIPTION OF THE PREFERRED EMBODIMENT OF THE PRESENT INVENTION

Figure 1:
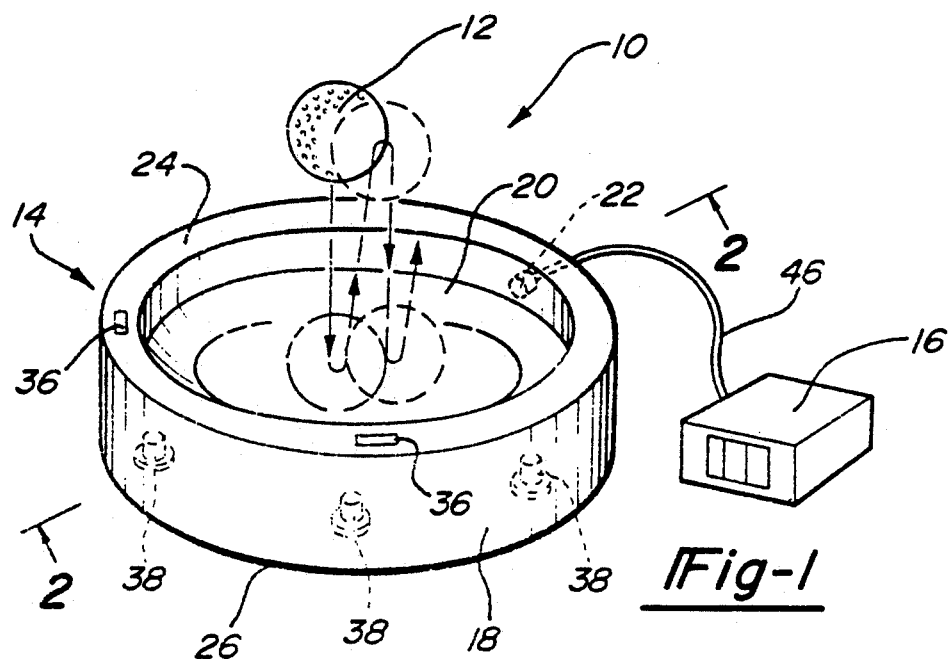
FIG. 1 is a perspective view of the preferred embodiment of the present invention.

With reference first to FIG. 1, a testing device 10 according to the present invention is thereshown. The testing device may be used to test any rebounding object, particularly, a ball for use in sporting events. The testing device 10 is particularly suited for use in testing a golf ball. Thus, set forth is a preferred embodiment of the invention for testing golf balls.

The coefficient of restitution e is defined as the ratio of the velocity of an object leaving a collision ($V_{out}$) to the velocity of approach ($v_{in}$) of the object to the collision. The value of e depends upon the shape and material property of the colliding bodies. In a perfectly elastic impact, the coefficient of restitution is unitary and there is no energy loss. A coefficient restitution of 0 indicates perfectly inelastic or plastic impact where there is no separation of the bodies after collision and the energy loss is a maximum. In oblique impact, the coefficient of restitution applies only to those components of velocity along a line of impact which are normal to the plane of impact.

Figure 5:
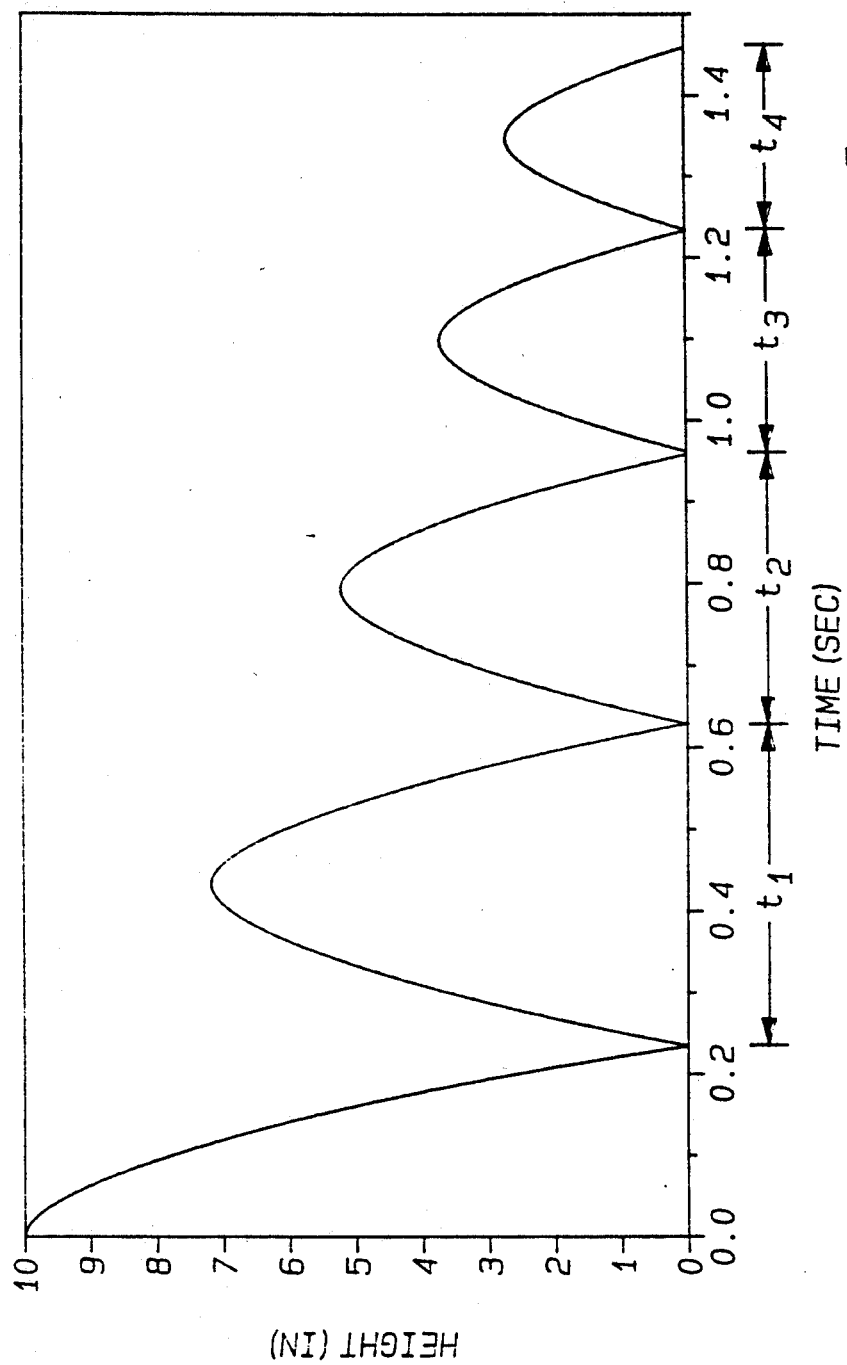
FIG. 5 is a chart illustrating the path of a ball bouncing over time.

The coefficient of restitution for a ball dropped against an object below may be measured if the mass of the object below has a mass which is very large in comparison to the mass of the ball. The path of a ball bouncing is shown in FIG. 5. The coefficient of restitution for the ball may then be expressed as:

$$V_{n+1} = e V_n \quad (1)$$

where $V_n$ is the downward velocity component before impact and $V_{n+1}$ is the upward velocity component after impact. As set forth in Greenwood, *Principled of Dynamics*, Prentice Hall 1965, a bounce period or time interval $t_n$ between the nth impact and the n+1 impact is $$t_n = \frac{2V_{n+1}}{g} = \frac{2eV_n}{g} \quad (2)$$

and from equations (1) and (2) the second or subsequent bounce period is $$t_{n+1} = \frac{2e}{g} V_{n+1} = \frac{2e^2}{g} V_n \quad (3)$$

and likewise the third bounce period is $$t_{n+2} = \frac{2e^2}{g} V_{n+1} = \frac{2e^3}{g} V_n \quad (4)$$

Comparing the second bounce period $t_2$ to the first bounce period $t_1$ from (2) and (3) as a ratio, results in the coefficient of restitution e $$\frac{t_2}{t_1} = \frac{t_{n+1}}{t_n} = \frac{\frac{2e^2}{g} V_n}{\frac{2e}{g} V_n} = e \quad (5)$$

Likewise, the coefficient of restitution may be determined by comparing the third bounce period $t_3$ to the second bounce period $t_2$.

$$\frac{t_3}{t_2} = \frac{t_{n+2}}{t_{n+1}} = \frac{\frac{2e^3}{g} V_n}{\frac{2e^2}{g} V_n} = e \quad (6)$$

Thus, when dropping a ball on an object having mass much greater than the ball and assuming no aerodynamic losses and a constant coefficient of restitution, the coefficient of restitution may be determined by comparing the bounce periods of any two successive bounces as follows:

$$e = \frac{t_{n+1}}{t_n} = \frac{t_2}{t_1} = \frac{t_3}{t_2} \ldots \quad (7)$$

Shown in FIG. 5, is a graph of a ball dropped from a height of 10 inches onto a reaction plate. From the following data it can be seen that coefficient of restitution may be computed as follows:

| IMPACT | TIME OF IMPACT | TIME DIFFERENCE | BOUNCE INTERVAL | $e \frac{t_{n+1}}{t_n}$ |
|---|---|---|---|---|
| 1 | 0.22751 | | | |
| 2 | 0.61427 | .38676 | $t_1$ | .85 |
| 3 | 0.94302 | .32875 | $t_2$ | .85 |
| 4 | 1.22245 | .27944 | $t_3$ | .85 |
| 5 | 1.45997 | .23752 | $t_4$ | .85 |

However, it can also be shown that if the coefficient of restitution e is determined by the ratio of successive bounce periods. In order to make such a determination an object must be permitted to impact and rebound from the reaction plate at least three times.

If the object is perfectly elastic, according to the law of conservation of energy, each subsequent bounce would be identical in height and duration as the proceeding bounce.

As shown in FIG. 5, the height and duration of each succeeding bounce is smaller. As shown above, the coefficient of restitution is also proportional to the ratio of a successive bounce period to a prior bounce period.

Shown in FIG. 1, is a testing device 10 for testing a golf ball 12 by measuring successive bounce periods of the ball. The testing device includes a bounce unit 14 and a display unit 16. The bounce unit 14 has a base 18, a reaction plate 20 and a transducer 22. The base is formed with a side wall 24 and bottom 26 defining a central bore for receiving the reaction plate 20. The base 18 may be formed of any suitable rigid material, such as wood or plastic.

The reaction plate 20 is disk-shaped having a dished top surface 30. The top surface 30 of the reaction plate should be smooth and is dished at its periphery to maintain the golf ball in the center of the reaction plate. The top surface has a centrally disposed flat center portion 32 and gradually sloped peripheral portion 34. The peripheral portion is angled upwardly from the flat portion at a slight angle, for instance, 1°.

Thus, in the case of the reaction plate for use with a golf ball, the reaction plate has a diameter of approximately 8 inches and the center portion has a diameter of approximately 4 inches. The peripheral portion 34 rises approximately 0.04 inches over the 2 inch distance between the center portion 32 and the outer circumference of the reaction plate 20 at an angle of approximately 1°. If the angle of the slope portion of the reaction plate is too great, the ball 12 will be deflected away from the reaction plate 20 so that it will not land on the reaction plate after it has rebounded from the plate.

The reaction plate 20 has great mass with respect to the ball 12. As is known, the ratio of the masses should be very large. The reaction plates are formed of a suitable dense material such as cast iron.

It has been found that a satisfactory mass for the reaction plate for use in testing a golf ball is approximately 11 pounds. A golf ball has a maximum weight of approximately 1.62 oz. Thus, the mass of the reaction plate is greater than 100 times the mass of the ball.

Figure 2:
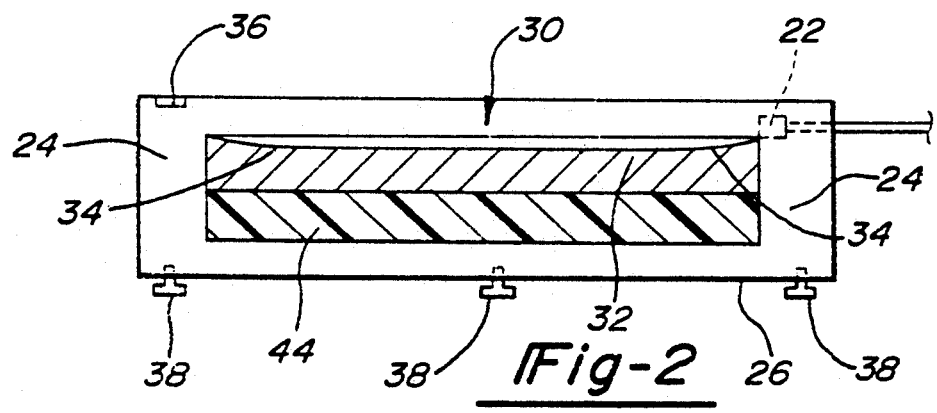
FIG. 2 is a cross-sectional view taken along line 2—2 of FIG. 1.

As shown in FIG. 2, the reaction plate 20 may be mounted on a pad 44 of foam material to mechanically isolate the plate from its foundation. Because the foundation may be a hard concrete surface or a soft carpeted surface, the pad material must have a low transmissibility so that variations in measurements of the coefficient of restitution are negligible from one installed location to the next. The pad 44 may be of any suitable low transmissibility material, such as an open celled foam or soft rubber In order to maintain the ball 12 on the reaction plate 20 as it is bouncing, the reaction plate should be aligned on a horizontal plane. The base may be provided with two bubble levels 36 for determining whether the plate is level, and a plurality of feet 38. The feet are threadably received in the bottom 26 of the base to facilitate the alignment of the reaction plate and base.

In the preferred embodiment, the side wall 24 of the base extends above the level of the top surface of the reaction plate to support the transducer 22 and to help maintain the ball on the reaction plate. The transducer 22 in the preferred embodiment is a small microphone. The microphone is mounted just above the impact surface and is directed at the reaction plate. However, the transducer may be any satisfactory type which will produce a signal upon impact of the ball on the reaction plate such as a piezoelectric strain gauge or accelerometer.

The transducer 22 positioned near the reaction plate 20 to detect each impact of the ball upon the reaction plate. As is set forth more fully below, the transducer is connected by a cable 46 to the display unit 16. Alternately, the display unit may be mounted directly upon the base and the transducer may be mounted in the base.

Figure 3:
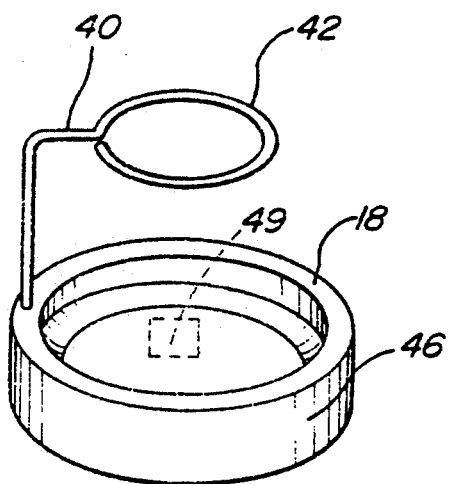
FIG. 3 is a perspective view of an alternative embodiment of the invention.

It has been found that the ball to be tested should be dropped from a sufficient height to provide sufficient velocity to permit the ball to bounce at least three times. In the case of a golf ball, this height has been found to be approximately 10 inches. It has been found that the device operates satisfactorily when the ball is dropped from any height above the minimum height necessary to produce three bounces. In order to insure that the ball is dropped on the center portion of the plate from a sufficient height, a guide 40, as shown in FIG. 3, may be provided. The guide is formed of wire having a loop 42 supported coaxially over the center portion 32 of the reaction plate 20 and spaced a predetermined distance, such as 10 inches, above the reaction plate.

It has also been found that the base unit may be used satisfactorily by merely placing the base unit on the floor and dropping a golf ball from an extended arm of the tester at a height of approximately 50 inches height equivalent to the waist of an average person. At this height, the ball will bounce sufficiently to permit calculating the coefficient of restitution and will not traverse away from the base unit as it rebounds.

Figure 4:
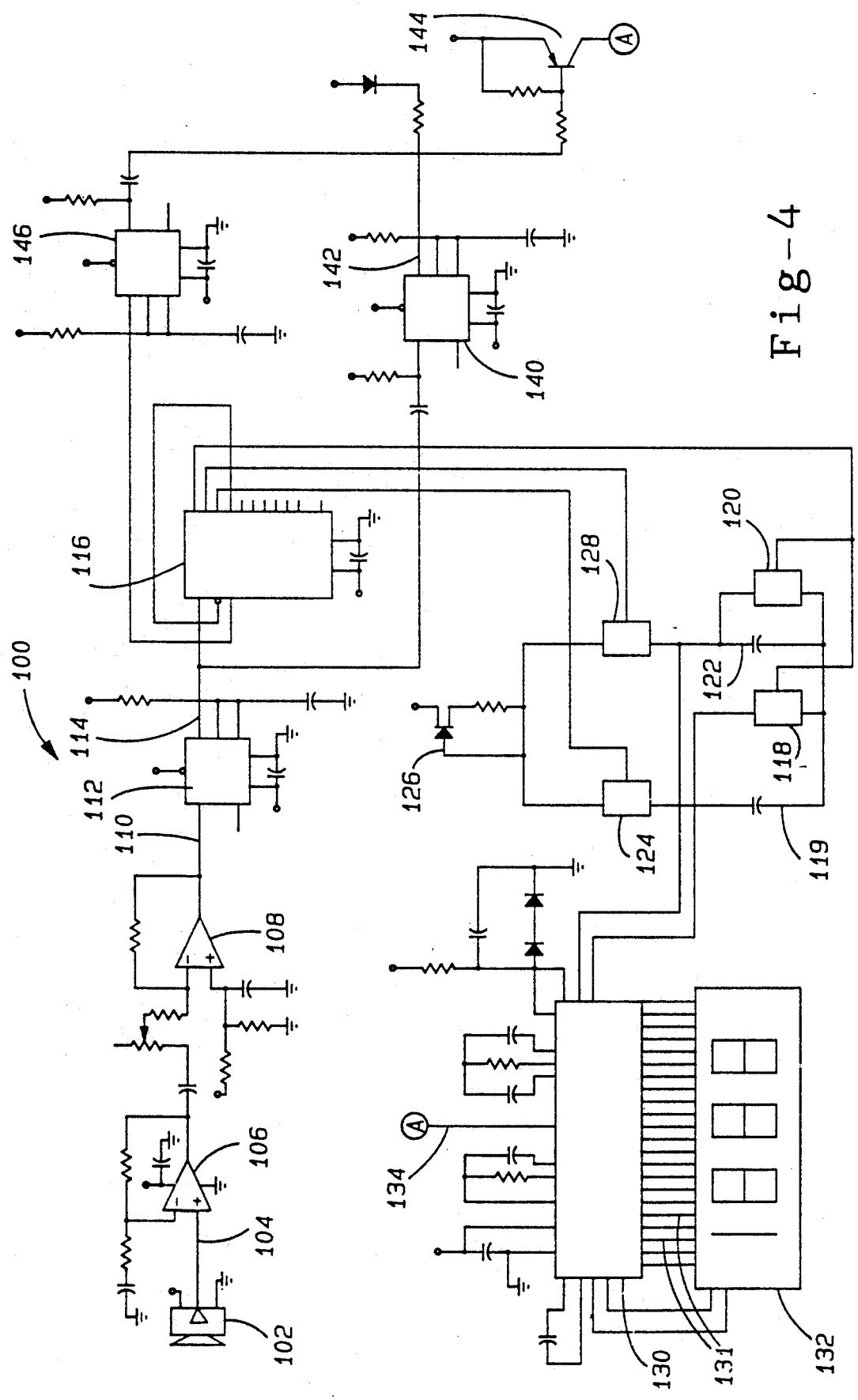
FIG. 4 is a schematic diagram of a circuit of the preferred embodiment of the present invention.

With reference now to FIG. 4, a schematic diagram of a circuit 100 for the preferred embodiment of the present invention is thereshown. The circuit 100 includes a transducer 102, such as a microphone, accelerometer, or a strain gauge, which detects each impact of a ball on the reaction plate 20 and generates a signal on its output 104 in response thereto.

The transducer output 104 is connected through two amplifiers 106 and 108 which are connected in series with each other and serve to amplify the output from the transducer 102. The output from the second amplifier 108 is coupled as an input signal to a trigger input 110 of a one shot multivibrator 112, such as a 555 timer.

In response to each output pulse from the amplifier 108, the multivibrator generates a square wave pulse of approximately 20 milliseconds in duration on its Q output 114. Thus, the multivibrator 112 serves to filter the amplified output from the multivibrator 112 and eliminate unnecessary and unwanted electric noise.

The Q output 114 from the timer 112 is connected to the clock input of a decade counter 116. The decade counter 116 has a plurality of outputs Q0-Q9 which sequentially change their state upon receipt of each input signal on the clock input from the multivibrator 112. Consequently, assuming that the output Q0 is active or high prior to the test, upon receipt of the first pulse from the clock input to the decade counter 116, Q0 goes low and Q1 goes high. The next clock input will change Q1 to a low state and Q2 to a high state and so forth. In the present embodiment of the invention, only Q0-Q3 are used.

The Q output from the decade 116 is connected at the control signal to two electronic switches 118 and 120. A first capacitor 119 is connected in parallel with the switch 118 while, similarly, a second capacitor 122 is connected in parallel with the second switch 120. Thus, when Q0 is high, both switches 118 and 120 are closed thus discharging any electric charge which may be present on either capacitor 119 or 122. Conversely, when Q0 goes low, each switch 118 and 120 opens thus allowing the capacitors 119 and 122 to charge in a fashion to be shortly described.

The Q1 output from the decade counter 116 is connected to the control input of an electronic switch 124 connected in series between a constant current source 126, and the capacitor 119. Similarly, the Q2 output from the decade counter 116 is connected as the control input to a further electronic switch 128 which is connected in series between the current source 126 and the second capacitor 122. Charging a capacitor with a constant current produces a voltage on the capacitor that is directly proportional to the time interval that the current is applied.

The capacitors 119 and 122 are respectively connected to the reference and input terminals of an A/D converter display driver 130. Outputs 131 from the display driver 130 are used to drive a conventional display unit 132, such as an LCD display. In the well known fashion, upon receipt of a display update signal on the hold input 134 of the display driver 130, the display driver 130 will display the ratio between the voltages of the reference and input terminals of the driver 130, and thus the ratio of the voltages on the capacitors 119 and 120.

In order to provide the hold signal on the hold input 134 to the display driver 130, a timer circuit 140, such as a 555 timer, is configured as a single shot multivibrator having a trigger input connected to the output from the first multivibrator 112. Thus, the timer circuit 140 generates a single pulse on its output 142 each time an input signal is received from the timer circuit 112, and thus each time the ball bounces on the reaction plate 20. This output 142 is connected to the base of a transistor 144 having its collector connected to the hold input 134 of the display driver. Thus, the display driver 134 receives a display update signal on its hold input 134 for each impact of a ball on the reaction plate 20.

A further timer circuit 146, such as a 555 timer, has its trigger input connected to the Q output 142 of the timer circuit 144. The timer circuit 146 generates a reset output signal to a reset input 148 of the decade counter 116 after a predetermined period, such as five seconds.

In operation, the transducer 102 detects each impact of the ball 12 on the reaction plate 20. The signal from the transducer 20, after amplification by the amplifiers 106 and 108, and wave shaping by the one shot multivibrator 112, increments the decade counter 116 for each impact of the ball.

During the time period from the first impact of the ball on the reaction plate to the second impact of the ball on the reaction plate, the electronic switch 128 is closed thus permitting the current source 126 to charge the capacitor 122. Conversely, during the interval between the second and third bounces of the ball on the reaction plate, the switch 124 is closed, thus allowing the current source 126 to charge the capacitor 119.

Consequently, after the third bounce, the actual voltage charges on the capacitors 119 and 122 are directly proportional to the time period between the first and second bounce and the second and third bounce, respectfully. The voltage from the capacitors 119 and 122 are electrically connected to the display driver 130 which displays the ratio on the LCD display 132 in the previously described fashion.

It should be apparent that other modifications and embodiments of the invention may be made without departing from the scope of the invention. Because the ratio of each subsequent bounce period to each proceeding bounce period is equivalent to coefficient of restitution e, the device could be modified to compare two or more pairs of bounce intervals and average the coefficients of restitutions resulting from each comparison. Likewise, the electronic circuitry could be simplified by the use of a microprocessor and other electronic components without departing from the scope of the invention.

The method of the invention utilizes the above-described testing device to determine the coefficient of restitution of a ball. It should be apparent that the method of the testing device disclosed may be used with any object which rebounds. However, the method is particularly suitable for use in the testing of balls and the like used in sporting events.

The method includes the first step of dropping the ball on a reaction plate from a height sufficient to permit the ball to rebound from the plate at least three times. As noted above, for a golf ball, a suitable minimum height is 10 inches. Below this height minimum, the ball may not have sufficient velocity to rebound from the plate. The reaction plate must have a mass which is much greater than the mass of the ball being dropped. The ratio will vary with the size and composition of the balls being tested, however, the ratio should be at least 50 to 1 and in the case of a golf ball, it has been found that the ratio of the mass of the plate to the ball advantageously has been found to be 100 to 1.

While the ball is bouncing on the reaction plate, the method further includes the step of detecting the impact of each bounce of the ball on the reaction plate with a transducer. The transducer may be a microphone, which detects noise produced by the collision, a strain gauge, or accelerometer which is affixed directly to the reaction plate. The reaction plate should be isolated from outside vibrations from the surface or foundation upon which the reaction plate is positioned. Additionally, the ball should be dropped vertically in order to insure the continued bouncing of the a ball upon the reaction plate and the reaction plate should be aligned horizontally to facilitate subsequent rebounding of the ball upon the reaction plate.

The next step of the method is timing a first bounce period and a subsequent bounce period occurring between three sequential impacts of the ball upon the reaction plate. The timing is triggered by signals produced by the transducer when the ball impacts the reaction plate.

As set forth above, the subsequent bounce period $t_{n+1}$ is compared with the preceding bounce period ti as a ratio to determine the coefficient of restitution e. Likewise, a third bounce period may be compared to a second bounce period, and so on. Multiple comparisons of successive bounce periods may be made and averaged. The display device may be provided with indicators such as lights which indicate balls having acceptable or non-acceptable values for the coefficient of restitution. Additionally, a coin activated power switch such as those used in vending machines may be provided.

Finally, the coefficient of restitution so generated is displayed in a suitable manner, such as using an LCD display.

I claim:

1. A testing device for determining the coefficient of restitution of a object having a predetermined mass, said object being freely dropped from a random position above said testing device, said testing device comprising:
   a reaction plate having a mass at least fifty times larger than said predetermined mass of said object, said reaction plate having a top surface having a portion aligned along a generally horizontal plane, said top surface being positioned below and spaced apart from said random position from where said object is dropped
   a transducer for detecting an impact upon said reaction plate, said transducer producing a signal in response to said impact;
   means for measuring at least two successive bounce periods of said object, each of said bounce periods being an interval of time between two successive impacts of said object on said reaction plate, said means for measuring being responsive to said signal produced by said transducer to measure said bounce periods and produce an output for each bounce period;
   means for storing said output for each bounce period; and means for computing the ratio of said output for a subsequent bounce period to said output for previous bounce period to determine said coefficient of restitution of said object.

2. The testing device of claim 1, further comprising means for displaying said coefficient of restitution.

3. The testing device of claim 1, further comprising a base for mounting said reaction plate.

4. The testing device of claim 3, further comprising a pad disposed between said base and said reaction plate for vibration isolation.

5. The device of claim 1, wherein said transducer further comprises a microphone for detecting noise produced by said impact.

6. The device of claim 1, wherein said transducer comprises a strain gauge mounted to said reaction plate.

7. The device of claim 1, wherein said reaction plate has a top surface having a flat portion disposed within an angled peripheral edge portion.

8. The device of claim 1, further comprising a means for positioning said ball for dropping on said reaction plate.

9. The device of claim 1, further comprising means for positioning said reaction plate on a horizontal plane.

10. A method of determining a coefficient of restitution of a ball, said method including the steps of:
   dropping a ball and permitting it to bounce at least three times on a reaction plate having a mass at least fifty times greater than the mass of said ball;
   detecting each impact of said ball on the reaction plate with a transducer;
   timing bounce periods of at least two sequential bounces of said ball with a timer responsive to a signal generated by said transducer, each bounce period being an interval of time between two successive bounces of said object;

comparing the bounce period of a subsequent bounce period to said first bounce period as a ratio to determining said coefficient of restitution; and displaying the coefficient of restitution.

11. The method of claim 10, further comprising the step of storing the output of said timer after said step of timing said bounce periods.

12. The device of claim 1, wherein said means for storing further comprises at least two capacitors.

13. The device of claim 1, wherein said transducer comprises an accelerometer mounted to said reaction plate.

* * * * *